(12) United States Patent
Shribbs et al.

(10) Patent No.: US 6,248,693 B1
(45) Date of Patent: Jun. 19, 2001

(54) HERBICIDAL COMPOSITIONS OF TETRAZOLINONE HERBICIDES AND ANTIDOTES THEREFOR

(75) Inventors: John M. Shribbs, Petaluma; Derek P. Dagarin, Richmond, both of CA (US)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 09/115,408

(22) Filed: Jul. 14, 1998

(51) Int. Cl.$^7$ .................................................. A01N 25/32
(52) U.S. Cl. ......................... 504/103; 504/105; 504/106; 504/108; 504/110; 504/112
(58) Field of Search ..................... 504/103, 112, 504/105, 106, 108, 110

(56) References Cited

U.S. PATENT DOCUMENTS

| | | | |
|---|---|---|---|
| 4,618,365 | 10/1986 | Covey et al. | 71/92 |
| 4,826,529 | 5/1989 | Covey et al. | 71/92 |
| 4,830,661 | 5/1989 | Covey et al. | 71/92 |
| 4,956,469 | 9/1990 | Covey et al. | 548/251 |
| 5,003,075 | 3/1991 | Covey et al. | 548/251 |
| 5,019,152 | 5/1991 | Covey et al. | 71/92 |
| 5,342,954 | 8/1994 | Goto et al. | 548/251 |
| 5,344,814 | 9/1994 | Goto et al. | 504/261 |
| 5,347,009 | 9/1994 | Goto et al. | 548/251 |
| 5,347,010 | 9/1994 | Goto et al. | 548/251 |
| 5,362,704 | 11/1994 | Goto et al. | 504/134 |
| 5,466,660 | 11/1995 | Goto et al. | 504/134 |
| 5,635,446 | 6/1997 | Goto et al. | 504/130 |

FOREIGN PATENT DOCUMENTS

| | | |
|---|---|---|
| 0 612 735 | 8/1994 | (EP) . |
| 0 672 663 | 9/1995 | (EP) . |
| 0 692 482 | 1/1996 | (EP) . |
| 0 695 748 | 2/1996 | (EP) . |
| 0 708 097 | 4/1996 | (EP) . |
| 0 711 761 | 5/1996 | (EP) . |

OTHER PUBLICATIONS

Devine et al. Physiology of Herbicide Action. Section 17.4: "Safeners for herbicides". p. 376–387, 1993.*

* cited by examiner

*Primary Examiner*—S. Mark Clardy
(74) *Attorney, Agent, or Firm*—Dianne Burkhard

(57) ABSTRACT

Herbicidal compositions containing tetrazolinone compounds and antidotal compounds therefor to reduce injury to various crops, particularly corn, wheat, rice and soya, from the phytotoxic effects of tetrazolinone herbicides when used alone or in combination with additional pesticidally active ingredients. Methods for reducing phytotoxicity or injury to crop plants, particularly corn and soya crops, due to tetrazolinone herbicides are also described.

17 Claims, No Drawings

HERBICIDAL COMPOSITIONS OF TETRAZOLINONE HERBICIDES AND ANTIDOTES THEREFOR

FIELD OF THE INVENTION

This invention relates to herbicide compositions and methods of use and, more particularly, to certain herbicidal compositions comprising tetrazolinone compounds and antidotes therefor which are useful as herbicides.

BACKGROUND OF THE INVENTION

An herbicide is a compound which adversely controls or modifies plant growth, e.g., killing, retarding, defoliating, desiccating, regulating, stunting, tillering, stimulating, and dwarfing. The term "plant" refers to all physical parts of a plant, including seeds, seedlings, saplings, roots, tubers, stems, stalks, foliage, and fruits. "Plant growth" includes all phases of development from seed germination to natural or induced cessation of life.

Herbicides are generally used to control or eradicate weed pests. They have gained a high degree of commercial success because it has been shown that such control can increase crop yield and reduce harvesting costs.

The most popular methods of herbicide application include: preplant incorporation into the soil; in-furrow application to seeds and surrounding soil; pre-emergence surface treatment of seeded soil; post-emergence treatment of the plant and soil; and preplant seed treatment.

A manufacturer of an herbicide generally recommends a range of application rates and concentrations calculated to maximize weed control. The range of rates varies from approximately 0.005 to 10 pounds per acre (0.0056 to 56 kilograms per hectare [kg/ha]), and is usually in the range of from 0.05 to 5 pounds per acre (0.056 to 5.6 kg/ha). The term "herbicidally effective amount" describes an amount of an herbicide compound which adversely controls or modifies plant growth. The actual amount used depends upon several considerations, including particular weed susceptibility and overall cost limitations.

An important factor influencing the usefulness of a given herbicide is its selectivity towards crops. In some cases, a beneficial crop is susceptible to the effects of the herbicide. In addition, certain herbicidal compounds are phytotoxic to some weed species but not to others. To be effective, an herbicide must cause minimal damage (preferably no damage) to the beneficial crop while maximizing damage to weed species which infest the locus of the crop.

To preserve the beneficial aspects of herbicide use and to minimize crop damage, many herbicide antidotes have been prepared. These antidotes reduce or eliminate damage to the crop without substantially impairing the damaging effect of the herbicide on weed species. See, for example, U.S. Pat. Nos. 4,021,224, 4,021,229 and 4,230,874.

Identification of an antidote which safens an herbicide in crops is a highly complicated task. The precise mechanism by which an antidote reduces herbicidal crop injury has not been established. An antidote compound may be a remedy, interferent, protectant, or antagonist. As used herein, "antidote" describes a compound which has the effect of establishing herbicide selectivity, i.e., continued herbicidal phytotoxicity to weed species by the herbicide, and reduced or non-phytotoxicity to the cultivated crop species. The term "antidotally effective amount" describes an amount of an antidote compound which counteracts to some degree a phytotoxic response of a beneficial crop to an herbicide.

Tetrazolinone compounds have been found to be very effective herbicides with broad general herbicidal activity against broad-leafed and grass weeds by pre- and/or post-emergence application. The method of controlling vegetation with these compounds comprises applying an herbicidally effective amount of the compounds, usually with an inert carrier or diluent, to the area where herbicidal control is desired. However, the herbicidal tetrazolinone compounds have been found in some instances to adversely affect or interfere with the cultivation of crop plants, especially corn and soya crops. Therefore, the effective use of these herbicides for controlling weeds in the presence of such crops is further enhanced by, or may require in many instances, the addition of an antidotally effective amount of a compound, which is antidotally effective with the herbicide.

It has now been discovered that certain compounds when used in an antidotally effective amount are effective antidotes for the protection of crops, especially corn, wheat, rice and soya, from adverse herbicidal injury or the reduction of adverse herbicidal injury caused by the use of an herbicidally effective amount of a tetrazolinone compound. Therefore, it is an object of the present invention to provide compositions of tetrazolinone herbicides in combination with antidotes therefor, which compositions are useful to reduce injury to crops, especially corn, wheat, rice and soya, due to phytotoxicity of these herbicides.

SUMMARY OF THE INVENTION

The present invention relates to herbicidal compositions comprising herbicidal tetrazolinone compounds and antidotal compounds therefor to reduce injury to various crops, particularly corn, wheat, rice and soya, from the phytotoxic effects of such tetrazolinone herbicides when used alone or in combination with other compounds as co-herbicides More particularly, the invention relates to a composition comprising:

(a) an herbicidal tetrazolinone, or an agriculturally acceptable salt thereof;

(b) an antidotally effective amount of an antidote compound which is antidotally effective with the herbicidal compound (a).

The invention further relates to methods for reducing phytotoxicity or injury to crop plants, particularly corn, wheat, rice and soya crops, due to an herbicidal tetrazolinone compound, or salt thereof, by applying an antidotally effective amount of an antidote compound to the soil, crop or crop seed.

DETAILED DESCRIPTION OF THE INVENTION

Tetrazolinone herbicide compounds useful in the present invention are described in U.S. Pat. Nos. 4,618,365; 4,826,529; 4,830,661; 4,956,469; 5,003,075; 5,019,152; 5,342,954; 5,344,814; 5,347,009; 5,347,010; 5,362,704 and 5,466,660 and in European Patent Publication No. 0 672 663 A1; 0 692 482 A2; 0 695 748 A1; 0 708 097 A1 and 0 711 761 A1 the disclosures of which are incorporated herein by reference. Herbicidal tetrazolinone compounds for use in this invention may be prepared by the methods described in the aforementioned patent publications, or by the application and adaptation of known methods used or described in the chemical literature.

Many herbicidal tetrazolinone compounds useful in this invention fall within the general formula

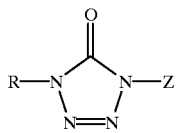
(I)

wherein:

R is hydrogen, optionally substituted $C_1$–$C_{12}$ alkyl, optionally substituted $C_2$–$C_{13}$ alkoxyalkyl, optionally substituted $C_1$–$C_{12}$ haloalkyl, optionally substituted $C_7$–$C_9$ aralkyl, optionally substituted $C_5$–$C_6$ cycloalkyl, optionally substituted $C_3$–$C_{12}$ alkenyl, optionally substituted aryl, or optionally substituted heteroaryl;

Z is hydrogen, $C_1$–$C_5$ alkylcarbonyl, $C_2$–$C_5$ alkoxycarbonyl, $S(O)_n$ optionally substituted phenyl or $C(O)NR^1R^2$ wherein $R^1$ and $R^2$ are the same or different and are selected from the group consisting of: hydrogen, optionally substituted $C_1$–$C_6$ alkyl, optionally substituted $C_3$–$C_6$ alkenyl, optionally substituted $C_5$–$C_6$ cycloalkyl and optionally substituted $C_7$–$C_9$ aralkyl; n is 0, 1 or 2; or $R^1$ and $R^2$ together with the nitrogen to which they are attached form an optionally substituted saturated or unsaturated 5 or 6 membered heterocyclic ring wherein the ring members are selected from nitrogen, carbon, oxygen and sulfur; or an agriculturally acceptable salt thereof which possesses herbicidal properties.

Compounds of formula I(a) are among the more preferred class of compounds

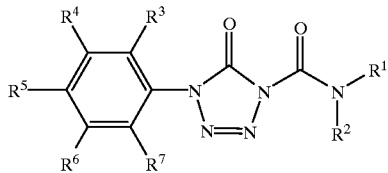
I(a)

wherein $R^1$ and $R^2$ are either the same or different and are selected from the group consisting of hydrogen, optionally substituted $C_1$–$C_{12}$ alkyl, optionally substituted $C_3$–$C_6$ alkenyl, optionally substituted $C_2$–$C_{13}$ alkoxyalkyl, optionally substituted $C_1$–$C_{12}$ haloalkyl and optionally substituted $C_5$–$C_6$ cycloalkyl; and $R^3$, $R^4$, $R^5$, $R^6$ and $R^7$ are either the same or different and are selected from the group consisting of hydrogen, halogen, optionally substituted $C_1$–$C_{12}$ alkyl, optionally substituted $C_2$–$C_{13}$ alkoxyalkyl, optionally substituted $C_1$–$C_{12}$ haloalkyl and optionally substituted $C_5$–$C_6$ cycloalkyl.

Preferred compounds are those in which $R^1$ and $R^2$ are the same or different and are selected from the group consisting of hydrogen, $C_1$–$C_6$ alkyl, $C_3$–$C_6$ alkenyl, $C_1$–$C_{12}$ haloalkyl and $C_5$–$C_6$ cycloalkyl; and $R^3$, $R^4$, $R^5$, $R^6$ and $R^7$ are selected from the group consisting of hydrogen, halogen, $C_1$–$C_6$ alkyl, and $C_1$–$C_{12}$ haloalkyl.

Especially preferred compounds have the following formula I(b):

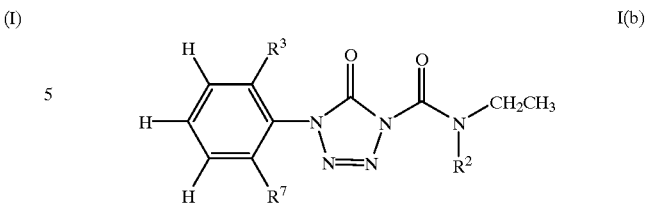
I(b)

wherein $R^3$ is chloro or ethyl; $R^7$ is hydrogen or chloro and $R^2$ is ethyl or cyclohexyl; or an agriculturally acceptable salt thereof.

By the term "agriculturally acceptable salts" is meant salts the cations or anions of which are known and accepted in the art for the formation of salts for agricultural or horticultural use. Preferably the salts are water-soluble. Suitable acid addition salts, formed by compounds of formula (I) containing an amino group, include salts with inorganic acids, for example, hydrochlorides, sulphates, phosphates and nitrates and salts with organic acids, for example, acetic acid. Suitable salts formed by compounds of formula (I) which are acidic, i.e., compounds containing one or more carboxy groups, with bases include alkali metal (e.g. sodium and potassium) salts, alkaline earth metal (e.g. calcium and magnesium) salts and ammonium and amine (e.g. diethanolamine, triethanolamine, octylamine, dioctylmethylamine and morpholine) salts.

As employed herein, the word "substituted" is intended to mean that the "substituted" group has one or more of the following substituents: halogen (i.e., fluorine, chlorine, bromine and iodine); $C_1$–$C_4$ alkyl; $C_1$–$C_4$ alkylthio; $C_1$–$C_4$ alkoxy; $(C_1$–$C_4)$alkoxy-$(C_1$–$C_4)$alkyl; $(C_1$–$C_6)$ alkoxyCO—; $C_1$–$C_4$ alkyl-$S(O)_p$—; nitro; nitrile; cyano; carboxy and salts, amides and esters thereof; alkanoyl of 2 to 4 carbon atoms; amino optionally substituted with one or two $C_1$–$C_4$ alkyl; phenyl optionally substituted with one or more $C_1$–$C_4$ alkyl, $C_1$–$C_4$ alkoxy, $C_1$–$C_4$ alkyl-$S(O)_p$—, nitro, halogen, fluorine, chlorine, bromine, cyano, or $CF_3$ groups; a five or six membered heterocyclic ring containing one or more heteroatoms selected from O, N or S; a five or six membered heterocyclic ring containing one or more heteroatoms selected from O, N or S optionally substituted with one or more $C_1$–$C_4$ alkyl, $C_1$–$C_4$ alkoxy, $C_1$–$C_4$ alkyl-$S(O)_p$—, nitro, halogen, fluorine, chlorine, bromine, cyano, or $CF_3$ groups; wherein p is 0, 1 or 2.

The term "optionally substituted aryl" is intended to include aryl groups, such as phenyl, naphthyl, benzyl and phenoxy which are unsubstituted or are substituted with one or more of the foregoing substituents. Similarly, the term "optionally substituted heteroaryl" is intended to include heteroaryl groups, such as pyridyl, pyrimidyl, triazinyl, thienyl, furyl and thiazolyl, which are unsubstituted or are substituted with one or more of the substituents listed above.

In the above definitions, the term "halogen" includes fluoro, chloro, bromo, and iodo groups. In polyhalogenated groups, the halogens may be the same or different.

This invention embodies a two-part herbicidal system comprised of (a) a tetrazolinone herbicide as described hereinabove and (b) an effective antidote therefor. It has been found that such antidote compounds can be selected from a wide range of chemical substances that have been found to be effective as herbicide antidotes for the above-described tetrazolinone herbicides. The preferred compositions of this invention may include any one or more of such antidotes with the herbicides. The variety of crops on which the above-described herbicides is useful can be significantly broadened by the use of an antidote to protect one or more crops from injury therefrom and render the composition more selective against weeds.

Preferably, the compositions of the present invention comprise an antidotally-effective amount of a compound selected from:

amides of haloalkanoic acids;

substituted phenylpyrimidines;

α-[(cyanomethoxy)imino]benzeneacetonitrile;

α-[(1,3-dioxolan-2-ylmethoxy)imino]-benzeneacetonitrile;

O-[3-dioxolan-2-ylmethyl]-2,2,2-trifluoromethyl-4'-chloroacetophenone oxime;

benzenemethamine, N-[4-(dichloromethylene)-1,3-diotholan-2-ylidene]-α-methyl, hydrochloride;

diphenylmethoxy acetic acid, methyl ester;

1,8-naphthalic anhydride;

cloquintocet;

2-chloro-N-[1-(2,4,6-trimethylphenyl)ethenyl]acetamide; and ethylene glycol acetal of 1,1-dichloroacetone.

Amides of haloalkanoic acids have the generalized formula II

(II)

in which $R^{10}$ is a mono-or poly-haloalkyl group. The halogens may be variously chloro, bromo or iodo; chloro is the preferred halogen, and the preferred group for R in these compounds in general is dichloromethyl, $Cl_2CH—$, i.e., the compounds are amides of dichloroacetic acid. In such compounds the nitrogen is further substituted by at least one other functional group or forms a portion of a heterocyclic ring, as will be described below.

Antidotes of this type are described in a number of publications such as U.S. Pat. Nos. 4,021,224; 4,256,481; 4,294,764; 4,900,360; European Patent Application, Publication No. 104,495, International Patent Application WO 81/406, and British Patent 1,521,540. U.S. Pat. No. 4,021,224 contains a broad disclosure of such types of compounds and indicates a great many possibilities for mono- or di-substitution on the nitrogen atom.

One group of preferred antidotal compounds includes those according to formula (III) wherein $R^{10}$ is $C_{1-3}$ haloalkyl, $R^{11}$ and $R^{12}$ are independently $C_{2-4}$ alkenyl or haloalkenyl or 2,3-dioxolan-2-yl-methyl or $R^{11}$ and $R^{12}$ when combined form a $C_{4-10}$ saturated or unsaturated heterocyclic ring containing O, S and/or N atoms and which may be substituted with $C_{1-5}$ alkyl, haloalkyl, alkoxy, alkoxyalkyl or haloacyl groups. The preferred haloalkyl $R^{10}$ member in formula (II) is dichloromethyl. Preferred species in this group of antidotal compounds are N,N-diallyl-dichloroacetamide and N-(2-propenyl)-N-(1,3-dioxolanyl-methyl) dichloroacetamide.

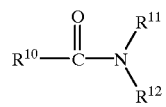

(III)

Still more preferred antidotal compounds according to formula (III) is a group of compounds in which $R^{10}$ is dichloromethyl and $R^{11}$ and $R^{12}$ taken together with this nitrogen atom fform an optionally substituted oxazolidine or thiazolidine ring. Compounds of this type have the general formula (IV):

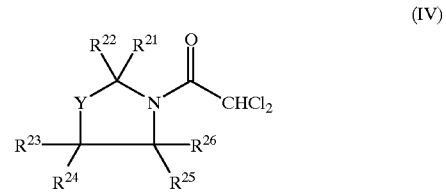

(IV)

wherein

Y is oxygen or sulfur;

$R^{21}$–$R^{26}$ are independently hydrogen; $C_{1-4}$ alkyl, alkylol, haloalkyl or alkoxy; $C_{2-6}$ alkoxyalkyl; $C_{1-4}$ alkylthio($C_{1-4}$) alkyl; $C_{1-4}$ alkylsulfonylmethyl; a bicyclic hydrocarbon radical having up to 10 carbon atoms; phenyl; or a saturated or unsaturated heterocyclic radical having 4–10 carbon ring atoms and containing O, S and/or N atom(s); wherein the phenyl and heterocyclic radicals are optionally substituted with one or more $C_{1-4}$ alkyl, $C_{1-4}$ haloalkyl, $C_{1-4}$ alkoxy, $C_{2-6}$ alkoxyalkyl, halogen or nitro radicals; or $R^{21}$ and $R^{22}$ together with the carbon atom to which they are attached form a $C_{3-7}$ spirocycloalkyl group optionally substituted by one or two methyl groups.

Preferred members according to formula (IV) are those wherein $R^{24}$, $R^{25}$ and $R^{26}$ are hydrogen; $R^{23}$ is hydrogen, methyl, phenyl or a heterocyclic radical; and $R^{21}$ and $R^{22}$ are independently methyl or trifluoromethyl, or when taken together with the carbon atom to which they are attached form a $C_5$ or $C_6$ spirocycloalkyl group.

Another type of haloalkanoic acid amide is disclosed in U.S. Pat. Nos. 4,601,745 and 4,618,361, and has the general formula

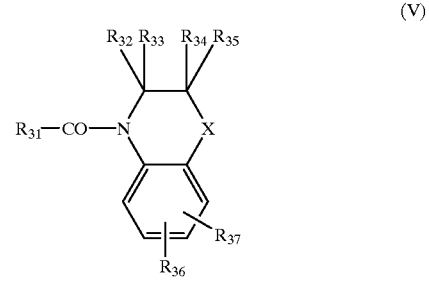

(V)

in which, among others, $R_{31}$ is $C_1$–$C_6$ haloalkyl, $R_{32}$–$R_{35}$ are independently hydrogen or $C_1$–$C_4$ alkyl, $R_{36}$ and $R_{37}$ are hydrogen, halogen, and a number of other substituents, and X is oxygen, sulfur, —SO— or —SO2. Preferably $R_{31}$ is dichloromethyl and X is oxygen. A preferred member of this group is 4-(dichloroacetyl)-3,4-benzoxazine ($R_1$=dichloromethyl; $R_2$=methyl; $R_3$–$R_7$=hydrogen; X—oxygen), also known as CGA-154281.

Substituted phenylpyrimidines are disclosed in U.S. Pat. No. 4,493,726 and have the general formula

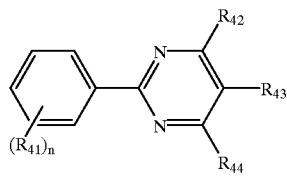

(VI)

in which $R_{41}$ is hydrogen or a number of substituents; n is an integer from 1 to 5; $R_{42}$ and $R_{44}$ are independently halogen or a number of substituents and $R_{43}$ is hydrogen, halogen, $C_1$–$C_6$ alkyl, $C_1$–$C_6$ haloalkyl or phenyl. One member of this group is 4,6-dichloro,2-phenylpyrimidine ($R_{41}$-hydrogen, $R_{42}$ and $R_{44}$=chlorine; $R_{43}$=hydrogen), also known as fenchorim or CGA-123407.

Diphenyl-methoxyacetic acid disclosed in U.S. Pat. No. 5,162,537 which is incorporated herein by reference. 1-(2-ethyl-6-methyl)phenyl phthalimide is disclosed in WO 96/15667 and has the following structure:

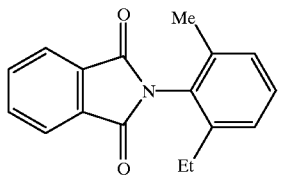

Finally, 3,3-diphenylpropionic acid is disclosed in commonly owned and co-pending application no. U.S. Ser. No. 08/812,953 which is incorporated herein by reference.

Especially preferred antidotes for use in the present invention include: 2,2,5-trimethyl-N-dichloroacetyl oxazolidine; 2,2-dimethyl-5-phenyl-N-dichloroacetyl oxazolidine; 2,2-dimethyl-5-(2-furanyl)-N-dichloroacetyl oxazolidine; 2,2-dimethyl-5-(2-thienyl)-N-dichloroacetyl oxazolidine; N,N-diallyl dichloroacetamide; 2,2-spirocyclohexy-N-dichloroacetyl oxazolidine; 2,2-dimethyl-N-dichloroacetyl oxazolidine; 4-(dichloroacetyl)-3,4-dihydro-3-methyl-2H-1,4-benzoxazine; 3-[3-(dichloroacetyl)-2,2-dimethyl-5-oxalidinyl]pyridine; 4-(dichloroacetyl)-1-oxa-4-azapiro-(4,5)-decane; 2,2-dichloro-1-(1,2,3,4-tetrahydro-1-methyl-2-isoquinolyl) ethanone; cis/trans-1,4-bis(dichloroacetyl)-2,5-dimethylpiperazine; N-(dichloroacetyl)-1,2,3,4-tetrahydroquinaldine; 1,5-bis(dichloroacetyl)-1,5-diazacyclononane; 1-(dichloroacetyl)-1-azaspiro[4,4]nonane; α-[(cyanomethoxy)imino]benzeneacetonitrile; α-[(1,3-dioxolan-2-ylmethoxy)imino]benzeneacetonitrile; O-[1,3-dioxolan-2-ylmethyl]-2,2,2-trifluoromethyl-4'-chloroacetophenone oxime; benzenemethamine, N-[4-(dichloromethylene)-1,3-diotholan-2-ylidene]-α-methyl hydrochloride;diphenylmethoxy acetic acid, methyl ester; 1,8-naphthalic anhydride;4,6-dichloro-2-phenylpyrimidine; 2-chloro-N-[1-(2,4,6-trimethylphenyl)ethenyl]-acetamide; cloquintocet; ethylene glycol acetal of 1,1-dichloroacetone; diphenylmethoxyacetic acid; 3,3-diphenylpropionic acid; 4,6-dichloro-2-phenyl-pyrimidine and 1-(2-ethyl-6-methyl) phenyl phthalimide.

Herbicidal compositions according to this invention may also contain one or more additional pesticidally active ingredients. Herbicides which may be used as co-herbicides with tetrazolinone compounds of formula (I) with benefit in combination with an antidote as described herein include, preferably, thiocarbamates (including dithiocarbamates), α-haloacetamides, heterocyclyl phenyl ethers, imidazolinones, pyridines and sulfonylureas. it is within the purview of this invention that other classes of herbicides, e.g., triazines, ureas, diphenyl ethers, nitroanilines, thiazoles, pyrrolidinones, aromatic and heterocyclic di- and triketones, etc., the individual members of which classes may be derivatives having one or more substituents selected from a wide variety of radicals may suitably be used a co-herbicides. Such combinations can be used to obtain selective weed control with low crop injury in several varieties of crop plants such as corn, grain sorghum, and cereals such as wheat, rice, barley, oats and rye, as well as several varieties of oil-seed crops such as soybeans and cotton. Insecticides, such as synthetic pyrethroids, fungicides, such as carbamates and triazoles and nematicides may also be included in the herbicidal compositions of this invention.

Effective weed control coupled with low crop injury is a result of treatment of a plant locus with a combination of an herbicidal tetrazolinone compound and an antidote compound in accordance with the present invention. By application to the "plant locus" is meant application to the plant growing medium, such as soil, as well as to the seeds, emerging seedlings, roots, stems, leaves, or other plant parts.

The phrase "combination of an herbicidal tetrazolinone compound and an antidote compound" includes various methods of treatment. For example, the soil of a plant locus may be treated with a "tank-mix" composition containing a mixture of the herbicide and the antidote which is "in combination." Or, the soil may be treated with the herbicide and antidote compounds separately so that the "combination" is made on, or in, the soil. After such treatments of the soil with a mixture of herbicide and antidote or by separate or sequential application of the herbicide and the antidote to the soil, the herbicide and antidote may be mixed into or incorporated into the soil either by mechanical mixing of the soil with implements or by "watering in" by rainfall or irrigation. The soil of a plant locus may also be treated with antidote by application of the antidote in a dispersible-concentrate form such as a granule. The granule may be applied to a furrow which is prepared for receipt of the crop seed and the herbicide may be applied to the plant locus either before or after in-furrow placement of the antidote-containing granule so that the herbicide and antidote form a "combination." Crop seed may be treated or coated with the antidote compound either while the crop seed is in-furrow just after seeding or, more commonly, the crop seed may be treated or coated with antidote prior to seeding into a furrow. The herbicide may be applied to the soil plant locus before or after seeding and a "combination" is made when both herbicide and an antidote-coated seed are in the soil. Also contemplated as a "combination" is a commercially-convenient association or presentation of herbicide and antidote. For example, the herbicide and antidote components in concentrated form may be contained in separate containers, but such containers may be presented for sale or sold together as a "combination." Or, the herbicide and antidote components in concentrated form may be in a mixture in a single container as a "combination." Either such a "combination" may be diluted or mixed with adjuvants suitable for soil applications. Another example of a commercially-presented combination is a container of antidote-coated crop seed sold, or presented for sale, along with a container of herbicide material. These containers may, or may not, be physically attached to each other, but nonetheless constitute a "combination of herbicide and antidote" when intended for use ultimately in the same plant locus.

In the foregoing description of various modes of application of the herbicide-antidote combinations, it is inherent that each form of application requires that in some manner, the herbicide and antidote will physically combine to form a "composition" of those agents.

The amount of a particular tetrazolinone herbicide to be applied to the plant locus or crop-growing area will vary with, inter alia, the nature of the weeds, the particular herbicide used, the time of application, the climate and the nature of the crop. Application rates of between about 0.01 kg/ha and 5.0 kg/ha of tetrazolinone herbicide are generally suitable, with a rate of about 0.1 kg/ha to 4.0 kg/ha being preferred, and about 0.1 kg/ha to 3.0 kg/ha being especially preferred.

The amount of a given antidote to be utilized in combination with the herbicide according to this invention and the manner of its utilization and resulting efficacy can vary according to various parameters, such as the particular antidote to be employed, the crop which is to be protected, the amount or rate of herbicide to be applied, and the soil and climatic conditions of the agricultural environment in which the combination is to be applied. The selection of a specific antidote for use in the herbicide composition, the manner in which it is to be applied (e.g., tank-mix, in-furrow application, seed treatment, etc.), the determination of activity which is non-phytotoxic but antidotally-effective, and the amount necessary to provide this result, can be readily performed utilizing the test procedures in the cited patents, such as U.S. Pat. No. 4,021,224, in accordance with common practice in the art.

For other descriptions of antidotes and methods of their use, reference is made to U.S. Pat. Nos. 3,959,304; 3,989,503; 3,131,509; 3,564,768; 4,137,070; 4,294,764; 4,256,481; 4,415,353; and 4,415,352.

The antidote is applied in combination with the herbicide in a non-phytotoxic antidotally effective amount. By "non-phytotoxic" is meant an amount of the antidote which causes at most minor or no injury to the desired crop species. By "antidotally-effective" is meant an antidote used in an amount which is effective as an antidote with the herbicide to decrease the extent of injury caused by the herbicide to the desired crop species.

The ratio of herbicide to antidote may vary depending upon the crop to be protected, weed to be inhibited, herbicide used, etc., but normally an herbicide-to-antidote ratio ranging from 1:25 to 60:1 parts by weight may be employed, although much higher rates of antidote may be used, e.g., 1:100 to 1:300 parts by weight of herbicide to-antidote. The preferred weight ratio of herbicide-to-antidote is from about 1:10 to about 30:1. Another preferred weight ratio range is from about 1:1 to about 20:1, with an even more preferred weight ratio range being from about 2:1 to about 15:1.

In field applications, the herbicide, antidote, or a mixture thereof, may be applied to the plant locus without any adjuvants other than a solvent. Usually, the herbicide, antidote, or mixture thereof, is applied in conjunction with one or more adjuvants in liquid or solid form. Compositions or formulations containing mixtures of an appropriate herbicide and antidote usually are prepared by admixing the herbicide and antidote with one or more adjuvants such as diluents, solvents, extenders, carriers, conditioning agents, water, wetting agents, dispersing agents, or emulsifying agents, or any suitable combination of these adjuvants These mixtures can be in the form of particulate solids, granules, pellets, wettable powders, dusts, solutions, aqueous dispersions, or emulsions.

Application of the herbicide, antidote, or mixture thereof, can be carried out by conventional techniques utilizing, for example, hand-carried or tractor-mounted spreaders, power dusters, boom and hand sprayers, spray dusters, and granular applicators. If desired, application of the compositions of the invention to plants can be accomplished by incorporating the compositions in the soil or other media.

The following examples are for illustrative purposes only and are not intended as necessarily representative of the overall testing performed and are not intended to limit the invention in any way. As one skilled in the art is aware, in herbicidal testing, a significant number of factors that are not readily controllable can affect the results of individual tests and render them non-reproducible. For example, the results may vary depending on environmental factors, such as amount of sunlight and water, soil type, pH of the soil, temperature, and humidity, among other factors. Also, the depth of planting, the application rate of the herbicide, the application rate of the antidote, and the ratio of the herbicide-to-antidote application, as well as the nature of crops being tested, can affect the results of the test. Results may vary from crop to crop within the crop varieties.

EXAMPLE I

The herbicide compound 1-(2,6-dichlorophenyl)-4-(N,N-diethyl carbamoyl)-5(4H)-tetrazolinone (cmp 1) and the antidote compound 2,2,5-trimethyl-N-dichloroacetyl oxazolidine (safener 1) were applied (at the rates listed in Table 1 below) preemergence to flats containing pasteurized, 2:1 loam: clay soil in which the following species had been sown: *Brachiaria platyphylla* (broadleaf signalgrass) ("BRAPP"); panicum miliaceum (white proso millet) ("PANMI"); *Digitaria sanguisalis* (hairy crabgrass) ("DIGSA"); *Setaria faberi* (giant foxtail) ("SETFA"); *Echinochloa crus-galli* (watergrass) ("ECHCG"); *Zea mays* (corn) ("Corn GA8532"). The soil was fortified with fertilizer (10-10-10) prior to seeding. All of the compounds applied were technical grade materials. The compounds were dissolved in 50/50 acetone/water solution and applied with a carrier volume of 200 L/ha. All treatments were replicated two times.

After application, flats were placed in a greenhouse and maintained under good growing conditions. Injury to plants was evaluated 21 days after treatment ("DAT"). Injury was evaluated as percent control, with percent control being the total injury to the plants due to all factors including: inhibited emergence, stunting, malformation, albinism, chlorosis, and other types of plant injury. The control ratings range from 0 to 100 percent, where 0% represents no effect with growth equal to the untreated control and where 100% represents complete kill. Results are sumarized in Table 1 below:

TABLE 1

| TREATMENT | | % PLANT INJURY | | | | | |
|---|---|---|---|---|---|---|---|
| CMP 1 (g/ha) | Safener 1 (g/ha) | BRAPP | PANMI | DIGSA | SETFA | ECHCG | Corn GA8532 |
| 125 | 100 | 79 | 83 | 99 | 100 | 30 | |
| 125 | 250 | — | — | — | — | 97 | 8 |

EXAMPLE II

The herbicide 1-(2-ethylphenyl)-4-(N,N-diethyl carbamoyl)-5(4H)-tetrazolinone (cmp 2) and the antidote compound N,N-diallyl dichloroacetamide (safener 2) were applied (at the rates listed in Tables 2 and 3 below) preemergence to flats or plastic cups containing pasteurized, 2:1 loam: clay soil into which the same species listed in Example I were sown. The soil was fortified with fertilizer (10-10-10) prior to seeding. All of the compounds applied were technical grade materials. The compounds were dissolved in 50/50 acetone/water solution and applied with a carrier volume of 200 L/ha. All treatments were replicated two times.

After application, flats were placed in a greenhouse and maintained under good growing conditions. Injury to plants was evaluated 20 days after treatment ("DAT"). Evaluation and rating was done as in Example I above.

TABLE 2

| TREATMENT | | % PLANT INJURY | | | | | |
|---|---|---|---|---|---|---|---|
| CMP 1 (g/ha) | Safener 1 (g/ha) | BRAPP | PANMI | DIGSA | SETFA | ECHCG | Corn GA8532 |
| 125 | 0 | 100 | 95 | 100 | 100 | 92.5 | — |
| 250 | 0 | 100 | 100 | 100 | 100 | 100 | 90 |
| 500 | 0 | — | — | — | — | — | 95 |
| 250 | 250 | — | — | — | — | — | 70 |
| 500 | 250 | — | — | — | — | — | 85 |

TABLE 3

| TREATMENT | | % PLANT INJURY | | | | | |
|---|---|---|---|---|---|---|---|
| CMP 2 (g/ha) | Safener 2 (g/ha) | BRAPP | PANMI | DIGSA | SETFA | ECHCG | Corn GA8532 |
| 125 | 0 | 100 | 93 | 100 | 100 | 100 | — |
| 250 | 0 | 100 | 100 | 100 | 100 | 100 | 10 |
| 500 | 0 | — | — | — | — | — | 25 |
| 250 | 250 | — | — | — | — | — | 0 |
| 500 | 250 | — | — | — | — | — | 0 |

EXAMPLE III

The following example describes a post flooding post emergence herbicidal screening test. Seeds of one weed specie were seeded into small pots. The pots were previously filled with clay soil which contained 2.2% organic matter and had a pH of 5.7. The weed specie was *Echinochloa crus-galli* ("ECHCG") at two growth stages (2-leaf and 3-leaf). In addition, the rice hybrid "Kosihikara" (*Oryza sativa*) was also seeded and the testing done at the 3-leaf stage.

The pots were placed into plastic tubs, lined with a plastic bag. The rice pots were placed into the tubs with the weed specie. The tubs were flooded with water to a depth of 2–3 cm above the pots.

The water inside the tubs was injected with the following antidote compounds diphenylmethoxyacetic acid (safener 3); 3,3-diphenylpropionic acid (safener 4); and 4,6-dichloro-2-phenyl-pyrimidine (safener 5) at a rate as indicated in Table 4. Next, the herbicide 1-(2-ethylphenyl)-4-(N,N-diethyl carbamoyl)-5(4H)-tetrazolinone (cmp 2) dissolved in acetone was injected at a rate of 0.063, 0.25, 0.50 and/or 1 kg per hectare. The degree of weed control was evaluated and recorded 27 days after treatment as a percentage of weed control as compared to the growth of the same species of the same age in an untreated control flat. Percent control is the total injury to the plants due to all factors including: inhibited emergence, stunting, malformation, albinism, chlorosis and other types of plant injury. The control ratings range from 0 to 100 percent, where 0 represents no effect with growth equal to the untreated control and where 100 represents complete kill. Representative results of the inventive compounds are shown in Table 4.

TABLE 4

| TREATMENT | | % PLANT INJURY | | |
|---|---|---|---|---|
| CMP 2 (g/ha) | Safener (g/ha) | ECHCG 2 leaf | ECHCG 3 leaf | ORYSA |
| 250 | None | 99 | 99 | 23 |
| 250 | Safener 3 (500 g/ha) | 100 | 92 | 5 |
| 250 | Safener 4 (750 g/ha) | 100 | 98 | 3 |
| 250 | Safener 5 (500 g/ha) | 100 | 98 | 14 |

As may be seen from the above tables, N,N-diallyl dichloroacetamide and 2,2,5-trimethyl-N-dichloroacetyl oxazolidine reduced corn injury 10 to 25%. In addition, rice injury was reduced 9–20% with the safeners employed.

EXAMPLE IV

The following example describes a post flooding, post emergence herbicidal screening test conducted similarly to Example III. The tubs were flooded 24 hours before application of the herbicides.

Herbicides used were compounds 1 and 2 and 1-(2-chlorophenyl)-4-(N-ethyl,N-cyclohexyl carbamoyl)-5(4H)-tetrazolinone (compound 3). Safeners used were safeners 3, 4 and 5 as in Example III.

Results are shown in Table 5.

TABLE 5

| TREATMENT | | % PLANT INJURY | | |
|---|---|---|---|---|
| Herbicide (g/ha) | Safener (g/ha) | ECHCG 2 leaf | ECHCG 3 leaf | ORYSA |
| CMP 1 250 g/ha | — | 100 | 100 | 73 |
| CMP 1 250 g/ha | Safener 3, (500 g/ha) | 100 | 100 | 38 |
| CMP 1 250 g/ha | Safener 4 (750 g/ha) | 100 | 100 | 2 |
| CMP 1 250 g/ha | Safener 5 (500 g/ha) | 100 | 100 | 45 |
| CMP 2 63 g/ha | — | 100 | 98 | 22 |
| CMP 2 63 g/ha | Safener 3 (500 g/ha) | 98 | 83 | 17 |
| CMP 2 63 g/ha | Safener 4 (750 g/ha) | 100 | 83 | 14 |
| CMP 2 63 g/ha | Safener 5 (500 g/ha) | 100 | 93 | 17 |
| CMP 3 2000 g/ha | — | 100 | 100 | 47 |
| CMP 3 2000 g/ha | Safener 3 (500 g/ha) | 100 | 100 | 22 |
| CMP 3 2000 g/ha | Safener 4 (750 g/ha) | 100 | 100 | 28 |
| CMP 3 2000 g/ha | Safener 5 (500 g/ha) | 100 | 100 | 48 |

As seen from the above data, the safeners reduced injury to rice from these herbicides.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

What is claimed is:

1. An herbicidal composition comprising:
   (a) an herbicially effective amount of an herbicidal tetrazolinone compound, or an agriculturally acceptable salt thereof; and
   (b) an antidotally effective amount of an antidote compound selected from dichloroacetyl oxazolidines, diphenylalkanoic acids, N, N-diallyl dichloroacetamide and 4,6-dichloro,2-phenylpyrimidine which is antidotally effective for said tetrazolinone.

2. An herbicidal composition according to claim 1, wherein component (a) is a tetrazolinone of the formula

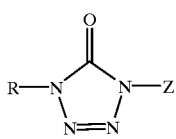

(I)

wherein:
R is hydrogen, optionally substituted $C_1$–$C_{12}$ alkyl, optionally substituted $C_2$–$C_{13}$ alkoxyalkyl, optionally substituted $C_1$–$C_{12}$ haloalkyl, optionally substituted $C_7$–$C_9$ aralkyl, optionally substituted $C_5$–$C_6$ cycloalkyl, optionally substituted $C_3$–$C_{12}$ alkenyl, optionally substituted aryl, and optionally substituted heteroaryl, Z is hydrogen, $C_1$–$C_5$ alkylcarbonyl, $C_2$–$C_5$ alkoxycarbonyl, S(O)$_n$ optionally substituted phenyl or C(O)NR$^1$R$^2$ wherein R$^1$ and R$^2$ are the same or different and are selected from the group consisting of: hydrogen, optionally substituted $C_1$–$C_6$ alkyl, optionally substituted $C_3$–$C_6$ alkenyl, optionally substituted $C_5$–$C_6$ cycloalkyl and optionally substituted $C_7$–$C_9$ aralkyl; n is 0, 1 or 2; or R$^1$ and R$^2$ together with the nitrogen to which they are attached form an optionally substituted saturated or unsaturated 5 or 6 membered heterocyclic ring wherein the ring members are selected from nitrogen, carbon, oxygen and sulfur; or an agriculturally acceptable salt thereof.

3. An herbicidal composition according to claim 2, wherein component (a) is a tetrazolinone of formula I(a)

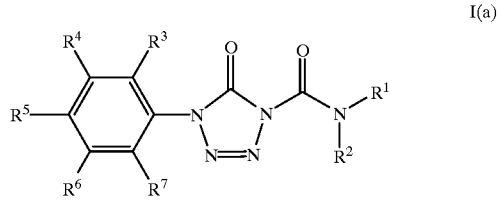

I(a)

wherein R$^1$ and R$^2$ are either the same or different and are selected from the group consisting of hydrogen, optionally substituted $C_1$–$C_{12}$ alkyl, optionally substituted $C_3$–$C_6$ alkenyl, optionally substituted $C_2$–$C_{13}$ alkoxyalkyl, optionally substituted $C_1$–$C_{12}$ haloalkyl and optionally substituted $C_5$–$C_6$ cycloalkyl; and R$^3$, R$^4$, R$^5$, R$^6$ and R$^7$ are either the same or different and are selected from the group consisting of hydrogen, halogen, optionally substituted $C_1$–$C_{12}$ alkyl, optionally substituted $C_2$–$C_{13}$ alkoxyalkyl, optionally substituted $C_1$–$C_{12}$ haloalkyl and optionally substituted $C_5$–$C_6$ cycloalkyl.

4. An herbicidal composition according to claim 2, wherein component (a) is a tetrazolinone of formula I(b)

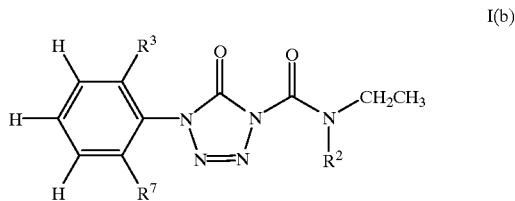

I(b)

wherein R$^3$ is chloro or ethyl; R$^7$ is hydrogen or chloro and R$^2$ is ethyl or cyclohexyl; or an agriculturally acceptable salt thereof.

5. An herbicidal composition according to claim 4 wherein component (a) is a tetrazolinone of formula I(b) wherein R$^3$ is chloro; R$^7$ is hydrogen and R2 is cyclohexyl; or an agriculturally acceptable salt thereof.

6. An herbicidal composition according to claim 4 wherein component (a) is a tetrazolinone of formula I(b) wherein R$^3$ is chloro; R7 is chloro and R2 is ethyl; or an agriculturally acceptable salt thereof.

7. An herbicidal composition according to claim 4 wherein component (a) is a tetrazolinone of formula I(b) wherein R$^3$ is ethyl; R7 is hydrogen and R2 is ethyl; or an agriculturally acceptable salt thereof.

8. An herbicidal composition according to claim 1, wherein component (b) is selected from the group consisting of 2,2,5-trimethyl-N-dichloroacetyl oxazolidine; 2,2-dimethyl-5-phenyl-N-dichloroacetyl oxazolidine; 2,2-dimethyl-5-(2-furanyl)-N-dichloroacetyl oxazolidine; 2,2-dimethyl-5-(2-thienyl)-N-dichloroacetyl oxazolidine; N,N-diallyl dichloroacetamide; 2,2-spirocyclohexy-N-dichloroacetyl oxazolidine; 2,2-dimethyl-N-dichloroacetyl oxazolidine; 4-(dichloroacetyl)-3,4-dihydro-3-methyl-2H-1,4-benzoxazine; 3-pyridine; 4,6-dichloro-2-phenylpyrimidine; 4,6-dichloro-2-phenyl-pyrimidine; diphenylmethoxyacetic acid; and 3,3-diphenylpropionic acid.

9. An herbicidal composition according to claim 1, wherein component (b) is selected from the group consisting of: 2,2,5-trimethyl-N-dichloroacetyl oxazolidine; 2,2-dimethyl-5-phenyl-N-dichloroacetyl oxazolidine; 2,2-dimethyl-5-(2-furanyl)-N-dichloroacetyl oxazolidine; 2,2-dimethyl-5-(2-thienyl)-N-dichloroacetyl oxazolidine; N,N-diallyl dichloroacetamide; 2,2-spirocyclohexy-N-dichloroacetyl oxazolidine; 2,2-dimethyl-N-dichloroacetyl oxazolidine; and 4-(dichloroacetyl)-3,4-dihydro-3-methyl-2H-1,4-benzoxazine.

10. A method of reducing injury to crops by a tetrazolinone herbicide which comprises applying to the soil, crop or seed an herbicidally effective amount of a tetrazolinone herbicide and a non-phytotoxic antidotally effective amount of an antidote selected from dichloroacetyl oxazolidines, diphenylalkanoic acids, N, N-diallyl dichloroacetamide and 4,6-dichloro,2-phenylpyrimidine which is antidotally effective for said tetrazolinone herbicide.

11. A method according to claim 10, wherein said antidote compound is selected from the group consisting of 2,2,5-trimethyl-N-dichloroacetyl oxazolidine; 2,2-dimethyl-5-phenyl-N-dichloroacetyl oxazolidine; 2,2-dimethyl-5-(2-furanyl)-N-dichloroacetyl oxazolidine; 2,2-dimethyl-5-(2-thienyl)-N-dichloroacetyl oxazolidine; N,N-diallyl dichloroacetamide; 2,2-spirocyclohexy-N-dichloroacetyl oxazolidine; 2,2-dimethyl-N-dichloroacetyl oxazolidine; 4-(dichloroacetyl)-3,4-dihydro-3-methyl-2H-1,4-benzoxazine; 3-pyridine; 4,6-dichloro-2-phenylpyrimidine; 4,6-dichloro-2-phenyl-pyrimidine; diphenylmethoxyacetic acid; and 3,3-diphenylpropionic acid.

12. A method according to claim 10, wherein said antidote compound is selected from the group consisting of: 2,2,5-trimethyl-N-dichloroacetyl oxazolidine; 2,2-dimethyl-5-phenyl-N-dichloroacetyl oxazolidine; 2,2-dimethyl-5-(2-furanyl)-N-dichloroacetyl oxazolidine; 2,2-dimethyl-5-(2-thienyl)-N-dichloroacetyl oxazolidine; N,N-diallyl dichloroacetamide; 2,2-spirocyclohexy-N-dichloroacetyl oxazolidine; 2,2-dimethyl-N-dichloroacetyl oxazolidine; and 4-(dichloroacetyl)-3,4-dihydro-3-methyl-2H-1,4-benzoxazine.

13. A method according to claim 10, wherein the crop is corn, wheat, rice or soya.

14. A method of reducing injury to crops by a tetrazolinone herbicide of the formula

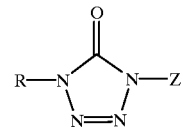

(I)

wherein:
R is hydrogen, optionally substituted $C_1$–$C_{12}$ alkyl, optionally substituted $C_2$–$C_{13}$ alkoxyalkyl, optionally substituted $C_1$–$C_{12}$ haloalkyl, optionally substituted $C_7$–$C_9$ aralkyl, optionally substituted $C_5$–$C_6$ cycloalkyl, optionally substituted $C_3$–$C_{12}$ alkenyl, optionally substituted aryl, or optionally substituted heteroaryl;
Z is hydrogen, $C_1$–$C_5$ alkylcarbonyl, $C_2$–$C_5$ alkoxycarbonyl, $S(O)_n$ optionally substituted phenyl or $C(O)NR^1R^2$ wherein $R^1$ and $R^2$ are the same or different and are selected from the group consisting of: hydrogen, optionally substituted $C_1$–$C_6$ alkyl, optionally substituted $C_3$–$C_6$ alkenyl, optionally substituted $C_5$–$C_6$ cycloalkyl and optionally substituted $C_7$–$C_9$ aralkyl; n is 0, 1 or 2; or
$R^1$ and $R^2$ together with the nitrogen to which they are attached form an optionally substituted saturated or unsaturated 5 or 6 membered heterocyclic ring wherein the ring members are selected from nitrogen, carbon oxygen and sulfur or an agriculturally acceptable salt thereof;
which comprises applying to the soil, crop or seed a non-phytotoxic antidotally effective amount of an antidote selected from dichloroacetyl oxazolidines, diphenylalkanoic acids, N, N-diallyl dichloroacetamide and 4,6-dichloro,2-phenylpyrimidine which is antidotally effective for said tetrazolinone herbicide.

15. A method according to claim 14, wherein said antidote compound is selected from the group consisting of 2,2,5-trimethyl-N-dichloroacetyl oxazolidine; 2,2-dimethyl-5-phenyl-N-dichloroacetyl oxazolidine; 2,2-dimethyl-5-(2-furanyl)-N-dichloroacetyl oxazolidine; 2,2-dimethyl-5-(2-thienyl)-N-dichloroacetyl oxazolidine; N,N-diallyl dichloroacetamide; 2,2-spirocyclohexy-N-dichloroacetyl oxazolidine; 2,2-dimethyl-N-dichloroacetyl oxazolidine; 4-(dichloroacetyl)-3,4-dihydro-3-methyl-2H-1,4-benzoxazine; 3-pyridine; 4,6-dichloro-2-phenylpyrimidine; 4,6-dichloro-2-phenyl-pyrimidine; diphenylmethoxyacetic acid; and 3,3-diphenylpropionic acid.

16. A method according to claim 14, wherein said antidote compound is selected from the group consisting of: 2,2,5-trimethyl-N-dichloroacetyl oxazolidine; 2,2-dimethyl-5-phenyl-N-dichloroacetyl oxazolidine; 2,2-dimethyl-5-(2-furanyl)-N-dichloroacetyl oxazolidine; 2,2-dimethyl-5-(2-thienyl)-N-dichloroacetyl oxazolidine; N,N-diallyl dichloroacetamide; 2,2-spirocyclohexy-N-dichloroacetyl oxazolidine; 2,2-dimethyl-N-dichloroacetyl oxazolidine; and (dichloroacetyl)-3,4-dihydro-3-methyl-2H-1,4-benzoxazine.

17. A method according to claim 14, wherein the crop is corn, wheat, rice or soya.

* * * * *